United States Patent [19]
Sarkki et al.

[11] Patent Number: 5,939,294
[45] Date of Patent: Aug. 17, 1999

[54] IMMOBILIZATION OF MICROOGRANISMS ON WEAKLY BASIC ANION EXCHANGE SUBSTANCE FOR PRODUCING ISOMALTULOSE

[75] Inventors: Marja-Leena Sarkki, Kantvik; Heikki Heikkila, Espoo; Tapio Viljava, Kantvik, all of Finland

[73] Assignee: Xyrofin Oy, Kotka, Finland

[21] Appl. No.: 08/857,808

[22] Filed: May 16, 1997

[51] Int. Cl.$^6$ .............................. C12P 19/12; C12N 11/02; C12N 11/12; C12N 11/08
[52] U.S. Cl. .................... 435/100; 435/177; 435/178; 435/179; 435/180
[58] Field of Search ...................................... 435/100, 174, 435/177, 180, 178, 179

[56] References Cited

U.S. PATENT DOCUMENTS

| | | | |
|---|---|---|---|
| 4,337,313 | 6/1982 | Hershberger et al. | 435/177 |
| 4,355,117 | 10/1982 | Antrim et al. | 321/28 |
| 4,359,531 | 11/1982 | Bucke et al. | 435/97 |
| 4,386,158 | 5/1983 | Shimizu et al. | 435/97 |
| 4,547,463 | 10/1985 | Sakafa et al. | 435/180 |
| 4,640,894 | 2/1987 | Munir | 435/100 |

FOREIGN PATENT DOCUMENTS

| | | |
|---|---|---|
| 0 028 900 | 5/1981 | European Pat. Off. . |
| 0 049 801 | 4/1982 | European Pat. Off. . |
| 0 077 971 | 5/1983 | European Pat. Off. . |
| 0160253 | 10/1986 | European Pat. Off. . |
| 0 200 069 | 12/1986 | European Pat. Off. . |
| 8102636 | 5/1982 | Finland . |

*Primary Examiner*—David M. Naff
*Attorney, Agent, or Firm*—Scully, Scott Murphy & Presser

[57] ABSTRACT

Isomaltulose-forming microorganisms are immobilized on a carrier that is a weakly basic anion exchange substance in the form of a substantially non-compressible porous particulate solid material, and are used for isomerization of sucrose to isomaltulose. A preferred carrier contains microfibers or microparticles of diethylaminoethyl cellulose adherently bound by agglomeration with polystyrene. The isomerization may be a continuous conversion in one or more columns packed with the carrier. Isomaltulose may be hydrogenated to form isomalt for use in sweetening. Microorganisms can be immobilized on the carrier by feeding microorganisms to a column containing the carrier. After microorganism immobilization, the carrier may be treated with a crosslinking and/or flocculating compound. Regeneration of the carrier is carried out by removing microorganisms, washing and reloading with fresh microorganisms.

16 Claims, No Drawings

IMMOBILIZATION OF MICROOGRANISMS ON WEAKLY BASIC ANION EXCHANGE SUBSTANCE FOR PRODUCING ISOMALTULOSE

FIELD OF THE INVENTION

The present invention relates to a process for the isomerization of sucrose into isomaltulose with the aid of viable immobilized isomaltulose-forming micro-organisms. The invention also relates to a carrier material comprising an anion exchange material and having immobilized thereon viable isomaltulose-forming micro-organism cells. The invention further relates to the production of isomalt from sucrose via isomaltulose.

BACKGROUND OF THE INVENTION

Isomaltulose (or palatinose) is a reducing disaccharide having the systematic name of 6-O-α-D-glucopyranosyl-D-fructofuranose. Isomaltulose has been proposed for use as a sweetener in the food industry and it is a raw material for the production of isomalt (palatinit) by hydrogenation. Isomalt is a substantially equimolar mixture of α-D-glucopyranosyl-(1,6)-sorbitol and α-D-glucopyranosyl-(1,6)-mannitol. Isomalt is a non-cariogenic special sweetener described as having a gentle sweetening flavour.

Various processes for the isomerization of sucrose to isomaltulose have been reported. The isomerization is believed to be performed by α-glucosyl transferase (saccharose mutase) enzyme which has been found to exist in micro-organisms such as *Protaminobacter rubrum, Serratica plymuthica, Erwinia rhapontici*, etc. The known isomerization techniques include isomerization with viable or dead micro-organism cells or with the enzyme in extracted form. Various techniques for the immobilization of the enzyme have also been reported.

Thus, for instance EP-B1-0 028 900 suggests immobilization of the enzyme of various isomerizing micro-organisms, preferably *E. rhapontici*. The preferred immobilization technique comprises entrapping dead microbe cells within calcium alginate pellets. Immobilization in a thick aqueous slurry of diethylaminoethyl cellulose (DEAE-cellulose) is also disclosed but is reported to provide poorer results.

U.S. Pat. No. 4,386,158 discloses improving the physical strength of calcium alginate gels used to immobilize α-glucosyl transferase by treatment with polyethyleneimine and glutaraldehyde.

U.S. Pat. No. 4,640,894 describes the production of isomaltulose by using a reactor including immobilized dead cells of *P. rubrum*. Various immobilization techniques, such as entrapment in gels and flocculation with flocculants are disclosed.

U.S. Pat. No. 4,373,313 and EP-B-0 077 971 disclose the immobilization of viable cells of *P. rubrum* by flocculation with tannin and a long chain polyamine, reaction with an adduct of epihalohydrin/polyamine copolymer and glutaraldehyde, and drying.

EP-B-0 049 801 discloses the immobilization of a sucrose converting enzyme isolated from *P. rubrum* on various carrier materials such as hollow fibers or cation exchange resins.

EP-B-0 200 069 discloses the selective immobilization of extracted saccharose mutase enzyme on an anionisable carrier material, especially a sulphonic acid cation-exchange matrix.

EP-A-0 160 253 discloses immobilization of *P. rubrum* cells through entrapment in a polymer system during polymerization to provide biocatalysts for the conversion of sucrose to isomaltulose.

The prior art processes for the conversion of sucrose to isomaltulose are not entirely satisfactory. The carrier material is generally produced on-site. The immobilization processes are complicated and care must be exercised not to harm the sensitive enzyme. Entrapping in alginate or carrageenan gels requires several separate process steps to be performed and a final cross-linking with glutaraldehyde is often necessary. The prior art flocculation with a flocculating agent in solution requires several subsequent production steps involving the enzyme, including drying, extrusion and granulation. Inclusion of the enzyme in a polymer during polymerization may provide a physically strong product but this process is also complicated and may affect the activity of the sensitive enzyme.

A further disadvantage associated with the prior art methods of including viable or dead micro-organism cells in a carrier during the production of the carrier matrix itself lies in the fact that when the activity has been lost, the whole carrier must be discarded.

SUMMARY OF THE INVENTION

An object of the present invention is to overcome disadvantages of the prior art techniques for immobilization of isomaltulose-forming microbes and to provide a technically feasible process for production of isomaltulose and isomalt from sucrose.

An object of the present invention is also to provide a process for converting sucrose to isomaltulose by immobilized viable micro-organisms without exposing the microbes to such reactions as are necessary for the production of a solid carrier body.

A further object of the invention is to provide a process, wherein immobilization of viable cells of an isomaltulose-forming micro-organism onto a carrier material is technically uncomplicated.

A further object of the invention is to provide a continuous process for converting sucrose to isomaltulose in a packed column, wherein the immobilized cells can be easily refreshed or re-activated during production.

An object of the invention is also to provide a process for producing isomaltulose in a packed column including a carrier having good physical strength and causing only a low pressure drop at flow of a sucrose solution through said columnn.

A specific object of the invention is to provide a process using a carrier system with isomaltulose-forming viable micro-organism cells, wherein the carrier can be regenerasted after use.

DETAILED DESCRIPTION OF THE INVENTION

It has surprisingly been found that a technically uncomplicated process for converting sucrose to isomaltulose by immobilized viable micro-organism cells can be provided by using as a carrier a solid porous material having weakly basic anion exchange properties.

The present invention is defined in the appended claims.

Accordingly, the invention relates to a process for the isomerization of sucrose into isomaltulose with the aid of viable isomaltulose-forming micro-organism cells immobilized on an anion exchange material. In said process a sucrose containing solution is contacted with said isomaltulose-forming micro-organism cells which have been immobilized on a porous particulate carrier material comprising a weakly basic anion exchange material in the form of an inert and substantially non-compressible solid matrix, whereafter the isomerization product is recovered from the solution.

The process of the invention may be performed either batch-wise or as a continuous process. A continuous process is preferably performed in a column packed with the carrier.

The viable micro-organism cells are preferably immobilized onto the surface of the porous carrier after the formation of the carrier matrix. The carrier may be either continuously or intermittently refreshed, for instance by feeding nutrients and/or growth medium through the column.

According to a specifically preferred embodiment the carrier material can be regenerated after use by removing all microbial cells, washing and reloading with fresh viable cells.

The present invention also relates to a process for the production of isomalt from sucrose, said process including the steps of contacting a sucrose containing solution with viable iso-maltulose-forming micro-organism cells immobilized on a porous particulate carrier material comprising a weakly basic anion exchange material in the form of an inert and substantially non-compressible solid matrix; hydrogenating said isomaltulose to isomalt; and recovering said isomalt.

The present invention also provides a carrier for use in a process for producing isomaltulose and/or isomalt from sucrose, said carrier comprising a porous particulate material comprising a weakly basic anion exchange material in the form of an inert and substantially non-compressible solid matrix having viable isomaltulose-forming micro-organism cells immobilized onto the surface thereof.

The term "isomaltulose-forming micro-organisms" as used in the present specification and in the claims is intended to mean any micro-organism which is capable of converting sucrose to isomaltulose and which can be immobilized onto the surface of a weakly basic anion exchange carrier material. Examples of such micro-organisms include, but are not limited to those mentioned in the above mentioned prior art patent specifications. A specially preferred micro-organism is *Protaminobacter rubrum* (CBS 574.77) since it is very effective and can safely be used for the production of food ingredients. Good results have also been obtained with, for instance, *Serratia ptymurhica* and *Erwinia rhapontici*, but these microbes have pathogenic properties and are therefore less safe to use. Other suitable isomaltulose-forming micro-organisms may also be isolated from sugar beets and similar sources or may be derived from such micro-organisms by various techniques, as is evident to those skilled in the art.

The anion exchange material useful as a carrier in the present invention should have an anion exchange capacity which renders it suitable for binding the viable microbial cells by adsorption. Weakly basic anion exchangers are preferred.

Weakly basic anion exchangers are materials having primary and/or secondary /or tertiary amino groups. They dissociate and have exchange capability in acidic solutions. The materials having tertiary amino groups have rather basic properties and they are also called medium basic anion exchangers.

The carrier should be inert in the sense that it should not affect the conversion of sucrose to isomaltulose. The carrier should, however, preferably promote the binding of the microbe cells to the surface thereof. The term "porous" as used of the carrier according to the invention is intended to mean that the solid carrier comprises a multitude of hollows and pores providing a surface area which is very large compared to, for instance, the surface area of a sphere having approximately the same radius.

The term "substantially non-compressible" as used in the specification and claims is intended to mean that the solid carrier does not deform to any appreciable extent at the pressure prevailing during the conversion process. This is a clear distinction from the deformable alginate gel pellets used in the prior art.

The carrier material of the invention should have a solid porous matrix capable of resisting deformation and allowing flow of the sucrose solution through the column without causing a large pressure drop.

Carrier materials which may be used according to the present invention are weakly basic anion exchangers in the form of solid granules or particles. Examples of commercially available carriers of this type are those used in the working examples of the present specification. The carrier material particles are preferably of a generally spherical form so as to provide less resistance to flow. The carrier material should also preferably be of a macro-porous nature for providing a large surface area.

The preferred carrier material of the present invention comprises a weakly basic anion exchange material in the form of diethylaminoethyl modified cellulose (DEAE cellulose) which includes microfibers or microparticles agglomerated with polystyrene, as described in U.S. Pat. No. 4,355,117, the disclosure of which is incorporated herein by reference.

The advantage of using a weakly basic anion exchanger in the form of a porous carrier material with a large surface area, is that the microbes will be immobilized on the surface of the carrier and not entrapped within the carrier material, as is the case with alginate gels and in situ formed polymers. The sucrose solution need not penetrate into the carrier itself and, thus, the conversion rate will be enhanced compared to systems wherein the microbes are entrapped within the carrier material.

The viable microbial cells are generally immobilized onto the carrier material on the conversion site. However, the carrier material may also be loaded with the microbial cells prior to use and the loaded carrier may be stored or transported for use at another location. One aspect of the present invention, in fact, concerns the porous solid carrier material including viable isomaltulose-forming micro-organism cells.

A third aspect of the invention concerns the production of isomalt by hydrogenation of the isomaltulose produced from sucrose by the conversion process using the immobilized viable micro-organism cells.

After the reaction in batch or column, the isomaltulose may be purified and recovered from the reaction solution. The isomaltulose may, for instance, be purified by ion-exchanging to remove impurities and by-products and crystallized by cooling crystallization. Isomalt can be produced from the isomaltulose by hydrogenation. The hydrogenation may, for instance, be performed as a catalytic hydrogenation in solution (30–50% w/w) using Raney nickel as a catalyst. The temperature is generally set at about 100 to 130° C., the hydrogen pressure at about 40 to 100 $kg/cm^2$, the process duration being from about 3 to 10 hours.

After completion of the hydrogenation the catalyst is separated from the reaction solution. The solution is filtered and, if desired, the resulting isomalt may be purified again by ion exchange. The isomalt may be used in liquid form or it may be recovered from the solution in ways which are well known to those skilled in the art. Alternatively, the isomaltulose may be hydrogenated into isomalt without a preceding crystallization and purification.

The process according to the invention for converting sucrose to isomaltulose may be performed as a batch-wise process in a reaction tank including the immobilized viable microbial cells on the particulate carrier. After a sufficient reaction time for conversion of up to 80% or more of the sucrose, the solid carrier may be removed from the solution by filtration. After the reaction the solution contains isomaltulose as the main reaction product, some trehalulose, fructose and glucose, as well as any unreacted sucrose.

In the preferred method the process is performed as a continuous process in a column packed with the carrier. There may be several columns which may be connected in series and/or in parallel, for instance for allowing one column to undergo regeneration while the other ones are in operation. The sucrose solution may also be recirculated through one or several columns to increase the conversion.

The carrier includes viable glucosyltransferase enzyme containing micro-organism cells (isomaltulose-forming micro-organism cells) immobilized onto the surface thereof. The immobilization of the microbes onto the carrier surface may be performed either through "on column loading" by feeding a cell suspension through a column packed with carrier; or "in shake flask loading" by introducing carrier to a cultivation medium during propagation in a shake flask or the like container.

In both methods it is preferable to further enhance the loading in column by feeding fresh nutrient medium through the column.

The "on column loading" allows the column to be packed with the new carrier material before any immobilization takes place. Loading with the microbes is easy and no additional reaction steps are necessary after the immobilization has taken place. Thus, the microbes are not exposed to any stringent treatment conditions.

If desired, the immobilization of the microbial cells onto the carrier may be enchanced by adding crosslinking agents such as glutaraldehyde to the solution. It is also possible to add flocculating agents such as those known in the prior art. Flocculation has been found to enchance the conversion and prolong the half life of the immobilized system. However, since the flocculation in the present invention is performed with the microbial cells immobilized on a solid carrier matrix, no drying step is required. The flocculated and crosslinked carrier is ready to use as such.

The reaction is preferably carried out in a packed column, at an optimal temperature of 25 to 35° C., preferably about 30° C. Temperatures of 35 to 45° C. have proven partly inactivating. Temperatures above 55° C. totally inactivated a *P. rubrum* column in 24 hours.

A solution containing sucrose in purified form or as molasses is made to flow through the packed column, preferably from bottom to top to facilitate the removal of $CO_2$, which will rise with the flow together with any aeration air to the top of the column.

The sucrose concentration of the solution should preferably be kept at about 20 to 40%, more preferably at 25 to 35%. Sucrose concentrations above 55% have been found to significantly reduce the conversion in a short space of time. The pH of the sucrose solution should preferably be kept at about 4 to 8, more preferably at 5.5 to 7.

Although the flow rate of the sucrose solution can be very slow to provide a very high conversion of sucrose to isomaltulose, a commercial process will preferably be operated at less than maximum conversion to save reactor volume. A conversion of up to about 80% is suitable in most applications. The isomerization may be continued until the isomaltulose yield drops. It may be preferable or necessary to refresh the microbial activity from time to time by feeding nutrients into the column. A constant low nutrient feed may also be used.

According to the preferred embodiment of the process according to the present invention the isomerization is performed as a continuous process in a packed column reactor containing immobilized microbial cells bonded to the surface of a substantially incompressible carrier having weakly basic anion exchange properties. The carrier is preferably composed of a continuous porous bed, or alternatively of dimpled or reticulated porous granules. The matrix or granules may be composed of individual microparticles or microfibres. This carrier structure provides a very large surface area for the immobilization of microbial cells.

The particulate or matrix character of the preferred carrier is produced by loosely binding, felting, weaving, gluing or agglomerating together the individual microparticles which comprise microfibres, microgranules, microspheres, microbeads, etc. The binding is accomplished by establishing chemical, adherent or mechanical links at some of the contact points between the individual microparticles. Chemical binding is accomplished by causing a chemical cross-linking reaction at these points. Adherent binding is accomplished by agglomerating or gluing the microparticles together through the use of an additional ingredient such as a thermoplastic resin. Mechanical binding is accomplished by entangling or knotting the fibres at the contact point or by joining the particles by meshing their surfaces together. In the latter form, the matrix will comprise a continuous structure throughout the reactor, much like cotton fluff of filter paper packed into a tube. Also in that case, in their final form, the particles will be discrete and individual.

The microparticles are composed of a weakly basic anion exchange substance that can be formed into the desired, rough-surfaced microparticles. These substances include native or regenerated cellulose or rayon that is derivatized to provide anion exchange character; synthetic anion exchange resins such as phenolformaldehyde resins, acrylic resins and polystyrene resins, as well as agarose or dextrin based anion exchange resins. The preferred carrier is a porous, particulate anion exchange substance derived from cellulose or rayon that has been chemically modified to provide anion exchange character. Especially preferred embodiments include microfibres or microparticles of diethylaminoethyl substituted cellulose, adherently bound by agglomeration with polystyrene.

It is believed that the electric forces established between the positively charged resin and the negatively charged microbial cells are primarily responsible for the binding of the microbe cells to the surfaces of the resin. This binding substantially reduces the leaching of the microbes, while still permitting intimate contact between the microbes and the sucrose solution.

Weakly basic anion exchangers of the above presented kind have proven especially advantageous in providing a stable and active carrier material for the conversion of sucrose to isomaltulose. These carriers are solid and non-deformable, which provides a long operation life and low resistance to flow. They have a large surface area, which allows a large microbial population per volume unit to be provided for the conversion.

A special advantage of the carrier system of the present invention is that when conversion drops after several refreshment cycles, the carrier may be regenerated, reloaded and taken into new use. This is especially so with the preferred carrier of the present invention, i.e. a DEAE-modified cellulose, comprising a solid polystyrene matrix. In case crosslinking with glutaraldehyde is performed, regeneration may, however, be complicated.

The invention will now be illustrated in detail with the following non-limiting examples.

EXAMPLE 1

Production of a carrier (DEAE) for immobilization
Granular derivatized cellulose was manufactured according to U.S. Pat. No. 4,355,117 as follows.

25 parts of fibrous cellulose was mixed with 25 parts of titanium dioxide and the mixture was compounded with 50 parts of food grade high-impact polystyrene using a twin-screw extruded. The extrudate was cooled in water, and sieved to a particle size of 0.35–0.85 mm.

The sieved granular agglomerated cellulose particles were derivatized to form DEAE cellulose as described in the above mentioned U.S. Patent.

20 g of the granular DEAE-cellulose produced was hydrated by soaking in distilled water for 5 hours. The hydrated DEAE-cellulose carrier was sanitized by soaking in ethanol (75%) for one hour and rinsed with sterile water before being transferred to a sterile glass column (60 cm high, 1,5 cm diameter).

Production of a Cell Suspension of *Protaminobacter rubrum* (CBS 574.77)

Cells from a culture of *Protaminobacter rubrum* strain (CBS 574.77) were diluted with 10 ml of saline. 0.1 ml aliquots of the resultant suspension were used to inoculate 300 ml of growth medium in 1000 ml sterilized shake flasks. The medium was as follows: sucrose 40 g/l, peptone 10 g/l, yeast extract 5 g/l, meat extract 3 g/l, $Na_2HPO_4$ 2 g/l, pH 7. The inoculated flasks 3×300 ml were shaken 230 rpm at 30° C. for 20 hours to reach concentration over $5 \times 10^9$ cells/ml.

Immobilization of the Bacteria on the DEAE-Cellulose Carrier 750 ml of the cell suspension were pumped through the carrier bed in column at a flow rate of 35 ml/h (=0.5 BV/h) at 25° C. from the top to the bottom. The amount of immobilized microbes in the column was enhanced by feeding the column with 750 ml of fresh growth medium after feeding the cell suspensions. The carrier in the column was now ready for the production stage.

Production of Isomaltulose in Column

A sucrose solution of 25% (pH 7.5) was fed at 30° C. continuously to the bottom of the column of immobilized *P. rubrum* on DEAE-cellulose carrier and product solution was removed from the top. This system allowed the $CO_2$ to be released and removed from the top of the column. Different conversions were achieved depending on the flow rate or sucrose concentration (see table below).

TABLE 1

| | Sucrose concentration 25% | | | |
|---|---|---|---|---|
| Flow rate (BV/h)* | 0.6 | 0.3 | 0.15 | 0.08 |
| isomaltulose | 12 | 22 | 35 | 61 |
| trehalulose | 1 | 2 | 2.5 | 4.5 |
| fructose | 1 | 2 | 2 | 2.5 |
| glucose | 1 | 1.5 | 1.5 | 2 |
| sucrose | 85 | 73 | 60 | 30 |

TABLE 1-continued

| | Flow rate 0.08 BV/h | | |
|---|---|---|---|
| Sucrose concentration | 25% | 35% | 55% |
| isomaltulose | 61 | 43 | 12 |
| trehalulose | 4.5 | 2 | 1 |
| fructose | 3 | 3 | 1 |
| glucose | 2 | 2.5 | 0.6 |
| sucrose | 30 | 50 | 86 |

(BV = Bed Volume)

The column of immobilized *P. rubrum* on DEAE-cellulose carrier was maintained in operation for two weeks. The conversion diminished as time went on. The immobilized cells were refreshed after two weeks by feeding the column with a fresh sterile cultivation medium (10 BV). After this refreshing cycle the flow rate of sucrose solution (25%, 30° C.) was adjusted to 0.08 BV/h which converted sucrose to the following product (analyzed by HPLC; ion exchange resin in $Pb^{++}$-form): isomaltulose 79%, trehalulose 0.9%, fructose 0.4%, glucose 0.6, sucrose 18.5%.

The isomaltulose solution received from the column of immobilized *P. rubrum* was evaporated at a temperature of 70–85° C. to the concentration of 70% and crystallized by linear cooling from 65° C. to 25° C. Isomaltulose crystals were recovered by centrifugation with washing and dried at 50° C. The centrifugation yield was 70% (isomaltulose from isomaltulose) and the isomaltulose content of the crystals was 95 to 100%.

Isomaltulose solution (50% w/w) was hydrogenated to isomalt using Raney nickel as a catalyst (pH 9, temperature 100° C., hydrogen pressure 40 $kg/cm^2$, 3 hours). After completion of the hydrogenation the Raney nickel was separated from the reaction solution. The solution was concentrated by evaporation and isomalt was crystallized from the solution in a conventional way.

After one month in use the DEAE-cellulose carrier was regenerated in column by washing out immobilized *P. rubrum* cells with 1 M NaOH (60° C.) until the original color of the carrier was achieved, washing with water, buffering to pH 5 and washing with sterile water. After that the carrier was ready for reloading and for a new production period.

EXAMPLE 2

Production of Cell Suspension of *Erwinia rhapontici* (ATCC 29284)

Cells from a culture of *Erwinia rhapontici* (ATCC 29284) were diluted with 10 ml of saline, 0.1 ml of aliquots of the resultant suspension were used to inoculate 300 ml of growth medium in 1000 ml sterilized shake flasks. The medium was as follows: sucrose 40 g/l, peptone 10 g/l, meat extract 6 g/l, $KH_2PO_4$ 0.01 M, pH 7. The inoculated flasks 3×300 ml were shaken 230 rpm at 30° C. for 24 hours to reach a concentration over $2 \times 10^9$ cells/ml.

Production of Cell Suspension of *Serretia plymuthica* (ATCC 15928)

Cells from a culture of *Serretia plymuthica* (ATCC 15928) were diluted with 10 ml of saline. 0.1 ml of aliquots of the resultant suspension were used to inoculate 300 ml of growth medium in 1000 ml sterilized shake flasks. The medium was as follows: sucrose 40 g/l, peptone 10 g/l, meat extract 6 g/l, $KH_2PO_4$ 0.01 M, pH 7. The inoculated flasks 3×300 were shaken 230 rpm at 30° C. for 24 hours to reach a concentration over $2 \times 10^9$ cells/ml.

Production of Isomaltulose in Column by Immobilized *Serretia plymuthica* (ATCC 15928) and *Erwinia rhapontici* (ATCC 29284)

Immobilization of *S.plymuthica* and *E.rhapontici* on a DEAE carrier, spezyme GDC (producer Cultor Ltd) was carried out as described in Example 1. A 25% sucrose (pH 7.5) solution was pumped at 30° C. continuously through the immobilized cell column. The flow rate was adjusted to maximize isomaltulose concentration in the outflow. Sucrose was converted to the following products (analyzed by HPLC; ion exchange resin in $Pb^{++}$-form);

| flow rate | *S. plymuthica* 0.12 BV/h | *E. rhapontici* 0.02 BV/h |
|---|---|---|
| isomaltulose | 80% | 79% |
| trehalulose | 7.5% | 15% |
| fructose | 5.5% | 0.5% |
| glucose | 3% | 0.5% |
| sucrose | — | —% |

Both columns with their specific immobilized microbial cells were maintained in operation for a couple of weeks. The production diminished as time went on. The microbes were refreshed from time to time by feeding the column with a fresh sterile cultivation medium (10 Bed Volume, BV).

Regeneration

After the several refreshing cycles (one month's use) the Spezyme GDC carrier was regenerated in column by washing out immobilized microbial cells with 1M NaOH (60° C.) until the original color of the carrier was achieved, washing with water and buffering to pH 5 and washing with sterile water. After that the carrier was ready for reloading and for a new production period.

EXAMPLE 3

Testing of Anion and Cation Exchange Resins

*Protaminobacter rubrum* (CBS 574.77) was cultivated in the same conditions as in Example 1. After 5 hours cultivation 3 grams of each tested ion exchange material was added to the 75 ml of the cultivation medium. Cultivation in shake flasks was continued up to 13 hours to load the ion exchange materials with cells of *P. rubrum*. The ion exchange materials were separated from the cultivation medium by filtration and washed with water. One of two Spezyme GDC carrier samples was exposed to glutaraldehyde treatment for cross-linking. 3 g of Spezyme GDC with immobilized *P. rubrum* was mixed with 15 ml of 0.3% glutaraldehyde. After 0.5 hour's slow agitation the Spezyme GDC was washed with 150 ml of distilled water. The activity of immobilized *P. rubrum* cells on each ion exchange material, including the glutaraldehyde treated Spezyme GDC, was determined as glucosyltransferase activity. The results of the tests are shown in Table 2. The properties of the carrier materials are shown in Table 3.

TABLE 2

The activity of *P. rubrum* cells immobilized on various carriers

| Ion exchanger | Solid matrix | Trade name | Glucosyl-transferase activity U/g |
|---|---|---|---|
| Weakly basic anion exchangers: | | | |
| DEAE-cellulose | polystyrene | Spezyme GDC[1] | 1.0 |
| DEAE-cellulose | polystyrene | Spezyme GDC + glutaraldehyde | 0.8 |
| tertiary amine | phenolform-aldehyde | Duolite A 568[2] | 1.3 |
| tertiary amine | styrene-di-vinyl-benzene | Amberlite IRA 93[2] | 0.6 |
| tertiary amine | polystyrene | Macronet MN-100[3] | 0.3 |
| Weakly acidic cation exchangers: | | | |
| carboxylic | polyacrylic | Duolite C 464[2] | 0 |
| Strongly basic anion exchangers: | | | |
| quaternary ammonium | polystyrene | Macronet MN 400[3] | 0 |
| quaternary ammonium | styrene-di-vinyl-benzene | Amberlite IRA 900[2] | 0 |
| Strongly acidic cation exchangers: | | | |
| sulphonic | polystyrene | Residion EXC[4] | 0 |
| sulphonic | styrene-di-vinylbenzene | Amberlite IRC 200[2] | 0 |

The ion exchangers were purchased from
[1]Cultor Ltd.
[2]Rohm et Haas Ltd.
[3]Purolite Ltd.
[4]Mitsubishi Chemicals Co

TABLE 3

Properties of the carrier materials

| | Capacity meq/ml | Surface $m^2/g$ | Pores Å |
|---|---|---|---|
| Weakly basic anion exchangers: | | | |
| Spezyme GDC-carrier | 0.2–0.25 | | |
| Duolite A 568 | 1.2 | 1 (ml/g) | 150–250 |
| Amberlite IRA 93 | 0.85 | 25 | 300–1000 |
| Macronet MN-100 | 0.15 | 800–1000 | 850–950 |
| Weakly acidic cation exchanger: | | | |
| Duolite C 464 | 2.7 | | |
| Strongly basic anion exchangers: | | | |
| Macronet MN 400 | 0.3 | 800–1000 | 850–950 |
| Amberlite IRA 900 | 1.0 | 18 | 100–1000 |
| Strongly acidic cation exchangers: | | | |
| Residion EXC | 1.1 | 200 | |
| Amberlite IRC 200 | 1.75 | 45 | 100–500 |

Determination of the Glucosyltransferase Activity

Incubation test: 5 ml of 10% sucrose solution in 0.05 M $KH_2PO_4$ buffer pH 7 was mixed with 1 g of the immobilisate in 5 ml of water in test tube. The mixture was incubated at 30° C. for 60 minutes shaking mildly. The enzyme reaction was stopped by heating the test tubes at 100° C. in a water bath for 2 minutes. A control sample was prepared likewise but the enzyme reaction was stopped directly after the addition of the enzyme sample. Isomaltulose formed in the reaction was determined as a reduced sugar (DNS-method). $U/g = (\mu Mol/ml \times 5\ ml)/(60\ min. \times amount\ of\ sample,\ g)$.

EXAMPLE 4

Production of a Cell Suspension of *Protaminobacter rubrum* (CBS 574.77)

Cells from a culture of *Protaminobacter rubrum* strain (CBS 574.77) were diluted with 10 ml of saline. 0.1 ml aliquots of the resultant suspension were used to inoculate 300 ml of growth medium in 1000 ml sterilized shake flasks. The medium was as follows: sucrose 40 g/l, peptone 10 g/l, yeast extract 5 g/l, meat extract 3 g/l, $Na_2HPO_4$ 2 g/l, pH 7.

The inoculated flasks 3×300 ml were shaken 230 rpm at 30° C. for 20 hours to reach a concentration over 5×10$^9$ cells/ml. The cell suspension was concentrated by centrifugation (5000 rpm, 20 min) to the volume of ⅛ of the original.

Immobilization of the Bacteria on a DEAE-Cellulose Carrier using Tannic Acid (TA), Polyethyleneimine (PEI) and Glutaraldehyde (GA)

A mixture of the above *P. rubrum* cell suspension and a Spezyme GDC carrier material (producer Cultor Ltd) was exposed to the following treatments:

1. 40 ml of the concentrated cell suspension and 20 ml of wet Spezyme GDC carrier were agitated with a magnetic stirrer at room temperature for 30 minutes.

2. 40 ml of the concentrated cell suspension and 20 ml of wet Spezyme GDC carrier were agitated with a magnetic stirrer at room temperature for 30 minutes. Thereafter 0.6 ml of a 10% glutaraldehyde (GA) solution was added to crosslink cells onto the Spezyme GDC carrier and agitation was continued for further 30 minutes.

3. 40 ml of the concentrated cell suspension and 20 ml of wet Spezyme GDC carrier were agitated with a magnetic stirrer at room temperature for 30 minutes. Thereafter 0.4 ml of polyethyleneiminie (PEI) (25%) was added to the same mixture to flocculate cells and mixing was continued for 10 minutes. The reaction mixture was crosslinked by adding 0.6 ml of glutaraldehyde (10%) to the mixture and agitation was continued for further 30 minutes. Granular type of flocculants appeared in the solution.

4. 40 ml of the concentrated cell suspension and 20 ml of wet Spezyme GDC carrier were agitated with a magnetic stirrer at room temperature for 30 minutes. Thereafter 1 ml of tannic acid (TA) (4%) was added to flocculate the cell suspension and the mixture was agitated for 30 minutes. Flocculation was further enhanced by adding 1 ml of PEI (25%) and by allowing the reaction to proceed for 10 minutes under agitation. Crosslinking of the flocs and the Spezyme GDC carrier was carried out by adding 0.6 ml of glutaraldehyde (10%) to the mixture and the agitation was continued for further 30 minutes. The solution comprised a mixture of Spezyme GDC granules containing adsorbed cells and agglomerated cells and separate granular flocs of cell mass.

Each one of the above four reaction mixtures 1 to 4 was transformed to its respective column (diameter 2 cm, volume 70 ml). Additional reaction solution was filtered off in the column through the Spezyme GDC and the granular flocs containing *P. rubrum* cells. Loading the column from the top with 32% sucrose solution in 0.05 M phosphate buffer (pH 7) at room temperature was started immediately at a feed rate of 4.4 ml/h (=0,25 BV/h). The conversion ability of each column was tested running the columns continuously for 20 days. The results are shown in Table 4 below.

TABLE 4

A summary of the column trials

|  | Trial 1 Spezyme | 2 Spezyme + GA | 3 Spezyme + GA + PEI | 4 Spezyme + TA + PEI + GA |
|---|---|---|---|---|
| isomaltulose yield % on d.s. (1st day) | 16 | 14 | 53 | 73 |
| isomaltulose production g/l (column)/ | | | | |

TABLE 4-continued

A summary of the column trials

|  | Trial 1 Spezyme | 2 Spezyme + GA | 3 Spezyme + GA + PEI | 4 Spezyme + TA + PEI + GA |
|---|---|---|---|---|
| h | | | | |
| after 1 day | 14 | 12 | 44 | 54 |
| after 20 days | 4.5 | 6 | 27 | 38 |
| half life, h (at 22–24° C.) | 250 | 500 | 800 | 850 |

The monitoring period of the column trials was 20 days and no changes in the resistance of flow was observed. The Spezyme GDC carrier had a combined effect as an immobilization carrier. It offered a good base for adsorbtion of the cells in solution and served as a flowing aid for the separate flocs.

The present invention has been described herein by way of some specific examples. These examples are, however, only of an illustrative nature and it is obvious to those skilled in the art that the invention may be varied in a number of ways without deviating from the scope of the appended claims.

We claim:

1. A carrier adapted for use in a microbial process, said carrier comprising a carrier material for the isomerization of sucrose into isomaltulose, said carrier being composed of a weakly basic anion exchange substance in the form of a substantially non-compressible porous particulate solid material and having viable isomaltulose-forming microorganism cells immobilized on the surface thereof.

2. A carrier according to claim 1, wherein said carrier includes a substance having anion exchange properties bound to a polymer matrix.

3. A carrier according to claim 2, wherein said carrier is an anion exchange material containing microfibers or microparticles of diethylaminoethyl (DEAE) modified cellulose adherently bound by agglomeration with polystyrene.

4. A process for the isomerization of sucrose into isomaltulose comprising:

(a) providing a carrier comprising a weakly basic anion exchange substance in the form of a substantially non-compressible porous particulate solid material;

(b) immobilizing viable isomaltulose-forming microorganism cells onto the surface of said carrier;

(c) contacting the immobilized micro-organism with a sucrose containing solution; and (d) recovering isomaltulose product from the solution.

5. A process according to claim 4, wherein said process is a continuous conversion process performed in one or more columns packed with said carrier.

6. A process according to claim 5, wherein said microorganism cells have been immobilized onto said carrier surface by feeding a microbe solution into said column(s).

7. A process according to claim 4, 2 or 3, wherein the microbial density on the carrier is increased by feeding immobilized micro-organism cells with a nutrient medium.

8. A process according to claim 4, wherein the microbial activity of the immobilized micro-organism cells is intermittently refreshed by feeding nutrient solution to the carrier.

9. A process according to claim 4, wherein the carrier is regenerated by removal of the micro-organism cells, washing and reloading with fresh viable micro-organism cells.

10. A process according to claim 4, wherein the carrier with said immobilized micro-organism cells is treated with a substance selected from compounds having crosslinking and/or flocculating properties.

11. A process according to claim 10, wherein said carrier with said immobilized micro-organism cells is treated with a substance selected from the group consisting of tannic acid, polyethyleneimine and glutaraldehyde.

12. A process according to claim 4, wherein the sucrose containing solution has a sucrose content of 20 to 40%.

13. A process according to claim 4, wherein said solid material of said carrier includes a substance having weakly basic anion exchange properties bound to a polymer matrix.

14. A process according to claim 4, wherein said carrier is an anion exchanger containing microfibers or microparticles of diethylaminoethyl (DEAE) modified cellulose adherently bound by agglomeration with polystyrene.

15. A process according to claim 4, wherein the sucrose containing solution has a sucrose content of 25 to 35%.

16. A process for the production of isomalt from sucrose comprising:
   (a) providing a carrier comprising a weakly basic anion exchange substance in the form of a substantially non-compressible porous particulate solid material;
   (b) immobilizing viable isomaltulose-forming micro-organism cells onto the surface of said carrier;
   (c) contacting the immobilized microorganism cells with a sucrose containing solution;
   (d) hydrogenating the resulting isomaltulose to isomalt; and
   (e) recovering said isomalt.

* * * * *

UNITED STATES PATENT AND TRADEMARK OFFICE
CERTIFICATE OF CORRECTION

PATENT NO. : 5,939,294
DATED : 8/17/99
INVENTOR(S) : Marja-Leena Sarkki

It is certified that error appears in the above-identified patent and that said Letters Patent is hereby corrected as shown below:

Title page, itme [54] and Col. 1, lines 1-4.

Please change title to --IMMOBILIZATION OF MICROORGANISMS ON AN ANION EXCHANGE SUBSTANCE FOR CONVERSION OF SUCROSE--

Signed and Sealed this

Twenty-ninth Day of August, 2000

*Attest:*

Q. TODD DICKINSON

*Attesting Officer*     *Director of Patents and Trademarks*

UNITED STATES PATENT AND TRADEMARK OFFICE
CERTIFICATE OF CORRECTION

PATENT NO. : 5,939,294　　　　　　　　　　　　　　　　　　　　　　　Page 1 of 1
DATED : August 17, 1999
INVENTOR(S) : M. Sarkki It is certified that error appears in the above-identified patent and that said Letters Patent is hereby corrected as shown below:

Title page,
Insert -- [30 Foreign Application Priority Data
　　　　May 17, 1996 (FI) ……………. 962095 --

Column 2,
Lines 53-54, "regenerasted" should read -- regenerated --

Column 12,
Line 51, after "isomaltulose" delete "product"

Signed and Sealed this

Third Day of September, 2002

Attest:

*Attesting Officer*

JAMES E. ROGAN
*Director of the United States Patent and Trademark Office*